(12) United States Patent
Graves et al.

(10) Patent No.: US 10,406,252 B2
(45) Date of Patent: Sep. 10, 2019

(54) SYSTEMS AND METHODS FOR AUTOCLAVE CART LOADING AND UNLOADING SYSTEM

(71) Applicant: Curium US LLC, St. Louis, MO (US)

(72) Inventors: Kevin B. Graves, Catawissa, MO (US); Bryan S. Petrofsky, St. Louis, MO (US); Sumit Verma, Chesterfield, MO (US); John Schmitz, St. Charles, MO (US); Michael J. D'Hooge, Bridgeton, MO (US)

(73) Assignee: Curium US LLC, St. Louis, MO (US)

( * ) Notice: Subject to any disclaimer, the term of this patent is extended or adjusted under 35 U.S.C. 154(b) by 176 days.

(21) Appl. No.: 15/410,017

(22) Filed: Jan. 19, 2017

(65) Prior Publication Data

US 2018/0200395 A1 Jul. 19, 2018

(51) Int. Cl.
| | | |
|---|---|---|
| *B66B 7/02* | (2006.01) | |
| *A23L 3/00* | (2006.01) | |
| *B65G 47/04* | (2006.01) | |
| *A61L 2/07* | (2006.01) | |
| *A61L 2/24* | (2006.01) | |

(Continued)

(52) U.S. Cl.
CPC .................. *A61L 2/07* (2013.01); *A61L 2/24* (2013.01); *A61L 2202/122* (2013.01); *A61L 2202/14* (2013.01); *G21F 1/08* (2013.01); *G21F 7/00* (2013.01); *G21G 1/0005* (2013.01)

(58) Field of Classification Search
CPC ........... A23L 3/001; B65G 47/04; B66B 7/02; A61L 2/07; A61L 2202/122
See application file for complete search history.

(56) References Cited

U.S. PATENT DOCUMENTS

| | | |
|---|---|---|
| 3,286,619 A | 11/1966 | Lee |
| 3,552,588 A | 1/1971 | Todd |

(Continued)

FOREIGN PATENT DOCUMENTS

| | | |
|---|---|---|
| CA | 673812 A | 11/1963 |
| DE | 102009042083 B3 | 4/2011 |

(Continued)

OTHER PUBLICATIONS

International Search Report and Written Opinion of the International Searching Authority regarding PCT/US2017/014131 dated Sep. 25, 2017; pp. 1-16.

*Primary Examiner* — Kevin Joyner
(74) *Attorney, Agent, or Firm* — Armstrong Teasdale LLP

(57) ABSTRACT

A system for manufacturing radionuclide generators including an enclosure defining a radioactive environment, at least one autoclave sterilizer within the enclosure, and at least two loading and unloading elevators. The enclosure includes radiation shielding to prevent radiation within the radioactive environment from moving to an exterior of the enclosure. Each autoclave sterilizer includes a plurality of sterilization stations arranged vertically and at least two autoclave rails. One loading and unloading elevator is configured to load a cart into the autoclave sterilizer and one loading and unloading elevator is configured to unload the cart from the autoclave sterilizer. Each loading and unloading elevator includes at least two cart rails configured to support the cart and a plurality of loading elevator rails coupled to the cart rails. The loading elevator rails are configured to adjust the height of the cart rails.

9 Claims, 9 Drawing Sheets

(51) Int. Cl.
    *G21G 1/00*     (2006.01)
    *G21F 1/08*     (2006.01)
    *G21F 7/00*     (2006.01)

(56) References Cited

U.S. PATENT DOCUMENTS

| | | |
|---|---|---|
| 3,776,257 A | 12/1973 | Piegza |
| 3,972,679 A | 8/1976 | Ruig |
| 3,986,832 A | 10/1976 | Smorenburg |
| 4,164,590 A | 8/1979 | Mencacci |
| 4,196,225 A | 4/1980 | Mencacci |
| 4,417,838 A | 11/1983 | Schultz et al. |
| 4,505,630 A | 3/1985 | Kaschner et al. |
| 4,525,978 A | 7/1985 | Hayase et al. |
| 4,646,629 A | 3/1987 | Creed et al. |
| 4,661,325 A | 4/1987 | Noro et al. |
| 4,666,722 A | 5/1987 | Creed et al. |
| 4,773,321 A | 9/1988 | Wijts |
| 4,773,807 A | 9/1988 | Kroll |
| 5,059,392 A | 10/1991 | Wijts |
| 5,358,030 A | 10/1994 | Veltman et al. |
| 5,422,130 A | 6/1995 | Fox et al. |
| 5,763,266 A | 6/1998 | Palsson et al. |
| 6,001,305 A | 12/1999 | Mueller |
| 6,149,366 A | 11/2000 | Deandrea |
| 6,582,960 B1 | 6/2003 | Martin et al. |
| 7,722,912 B2 | 5/2010 | Hotek et al. |
| 8,900,454 B2 | 12/2014 | Cirou et al. |
| 8,906,229 B2 | 12/2014 | Cirou et al. |
| 8,916,045 B2 | 12/2014 | Reinbigler et al. |
| 8,919,080 B2 | 12/2014 | Richter |
| 8,921,096 B2 | 12/2014 | Weissenbach et al. |
| 9,051,929 B2 | 6/2015 | Cirou et al. |
| 9,095,210 B1 | 8/2015 | Alspaugh |
| 9,174,145 B2 | 11/2015 | Weissenbach et al. |
| 9,174,171 B2 | 11/2015 | Weissenbach et al. |
| 9,181,941 B2 | 11/2015 | Cirou et al. |
| 9,205,955 B2 | 12/2015 | Cirou et al. |
| 9,259,687 B2 | 2/2016 | Weissenbach et al. |
| 2003/0040104 A1 | 2/2003 | Barbera-Guillem |
| 2006/0257552 A1 | 11/2006 | Hotek et al. |
| 2010/0187167 A1 | 7/2010 | Reinbigler et al. |
| 2010/0209590 A1 | 8/2010 | Hotek et al. |
| 2011/0067355 A1 | 3/2011 | Richter |
| 2012/0031510 A1 | 2/2012 | Weissenbach et al. |
| 2012/0138173 A1 | 6/2012 | Cirou et al. |
| 2013/0210130 A1 | 8/2013 | Larcher et al. |
| 2015/0284018 A1 | 10/2015 | Krosney |

FOREIGN PATENT DOCUMENTS

| | | |
|---|---|---|
| EP | 0075531 A2 | 3/1983 |
| EP | 0165172 B1 | 5/1988 |
| EP | 0832182 B1 | 8/2001 |
| EP | 0733309 B1 | 8/2002 |
| EP | 1571201 A2 | 9/2005 |
| GB | 2006511 A | 5/1979 |
| WO | 03087292 A2 | 10/2003 |
| WO | 03087292 A3 | 12/2003 |
| WO | 2005119186 A1 | 12/2005 |
| WO | 2013043992 A1 | 3/2013 |

SYSTEMS AND METHODS FOR AUTOCLAVE CART LOADING AND UNLOADING SYSTEM

FIELD

The field of the disclosure relates generally to radionuclide generators and, more particularly, to systems and methods for an autoclave rack loading system.

BACKGROUND

Radioisotopes used for medical diagnostic purposes may emit high levels of radioactivity. These radioisotopes are typically generated in generators contained within hot cells that prevent the radioactivity from escaping the generator. However, the hot cell prevents operators from accessing the generation process. Accordingly, equipment within the hot cell, such as autoclave sterilizers, must be loaded by automated equipment within the hot cell.

Conventional autoclaves include only one sterilization station or cart containing column assemblies. The sterilization process can take a significant amount of time such that he sterilization process may be the rate limiting step in the generation process. More sterilization stations within an autoclave increases the amount of column assemblies which can be sterilized in an autoclave. Because space is limited in autoclaves, more sterilization stations may be added to the autoclave by stacking the stations on top of each other. Raising carts of column assemblies to the stacked sterilization stations may be a challenge. Accordingly, a need exists for reliable automated systems and methods for loading carts of column assemblies into autoclaves with stacked sterilization stations.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

One aspect is a system for manufacturing radionuclide generators including an enclosure defining a radioactive environment, at least one autoclave sterilizer within the enclosure, and at least two loading and unloading elevators. The enclosure includes radiation shielding to prevent radiation within the radioactive environment from moving to an exterior of the enclosure. Each autoclave sterilizer includes a plurality of sterilization stations arranged vertically and at least two autoclave rails. One loading and unloading elevator is configured to load a cart into the autoclave sterilizer and one loading and unloading elevator is configured to unload the cart from the autoclave sterilizer. Each loading and unloading elevator includes at least two cart rails configured to support the cart and a plurality of loading elevator rails coupled to the cart rails. The loading elevator rails are configured to adjust the height of the cart rails.

In another aspect, a loading and unloading elevator for an autoclave sterilizer in a radioactive environment including a table top, an elevation system, at least two cart rails, and a plurality of loading elevator rails. The table top separates a processing space from a maintenance space. The elevation system is positioned within the maintenance space. The cart rails are configured to support a cart. The loading elevator rails are coupled to the cart rails. The cart rails are positioned within the processing space. The loading elevator rails extend from the elevation system within the maintenance space through the table top to the processing space. The loading elevator rails are configured to adjust the height of the cart rails.

In yet another aspect, a method includes transferring a cart to a first loading and unloading elevator within a radioactive environment. The cart is configured to hold a plurality of column assembly racks. Each column assembly rack is configured to hold a plurality of column assemblies. The first loading and unloading elevator includes at least two cart rails, a motor, and a plurality of loading elevator rails coupled to the cart rails. The cart rails are configured to support the cart. The loading elevator rails are configured to adjust the height of the cart rails. The method also includes adjusting the height of the cart with the motor to a predetermined height corresponding to the height of a sterilization station within an autoclave. The method further includes transferring the cart to the sterilization station.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

Radioactive material is used in nuclear medicine for diagnostic and therapeutic purposes by injecting a patient with a small dose of the radioactive material, which concentrates in certain organs or regions of the patient. Radioactive materials typically used for nuclear medicine include Technetium-99m ("Tc-99m"), Indium-111m ("In-111"), Thallium-201, and Strontium-87m, among others.

Such radioactive materials may be produced using a radionuclide generator. Radionuclide generators generally include an autoclave for terminally sterilizing column assemblies. The autoclave may be located in a hot cell to shield the surrounding environment from radiation. As such, space within the hot cell and the autoclave is limited. In order to maximize the space within the autoclave, racks of column assemblies are stacked vertically within the autoclave. A loading and unloading system loads the racks into the autoclave and unloads the racks from the autoclave after sterilization.

Figure 1:
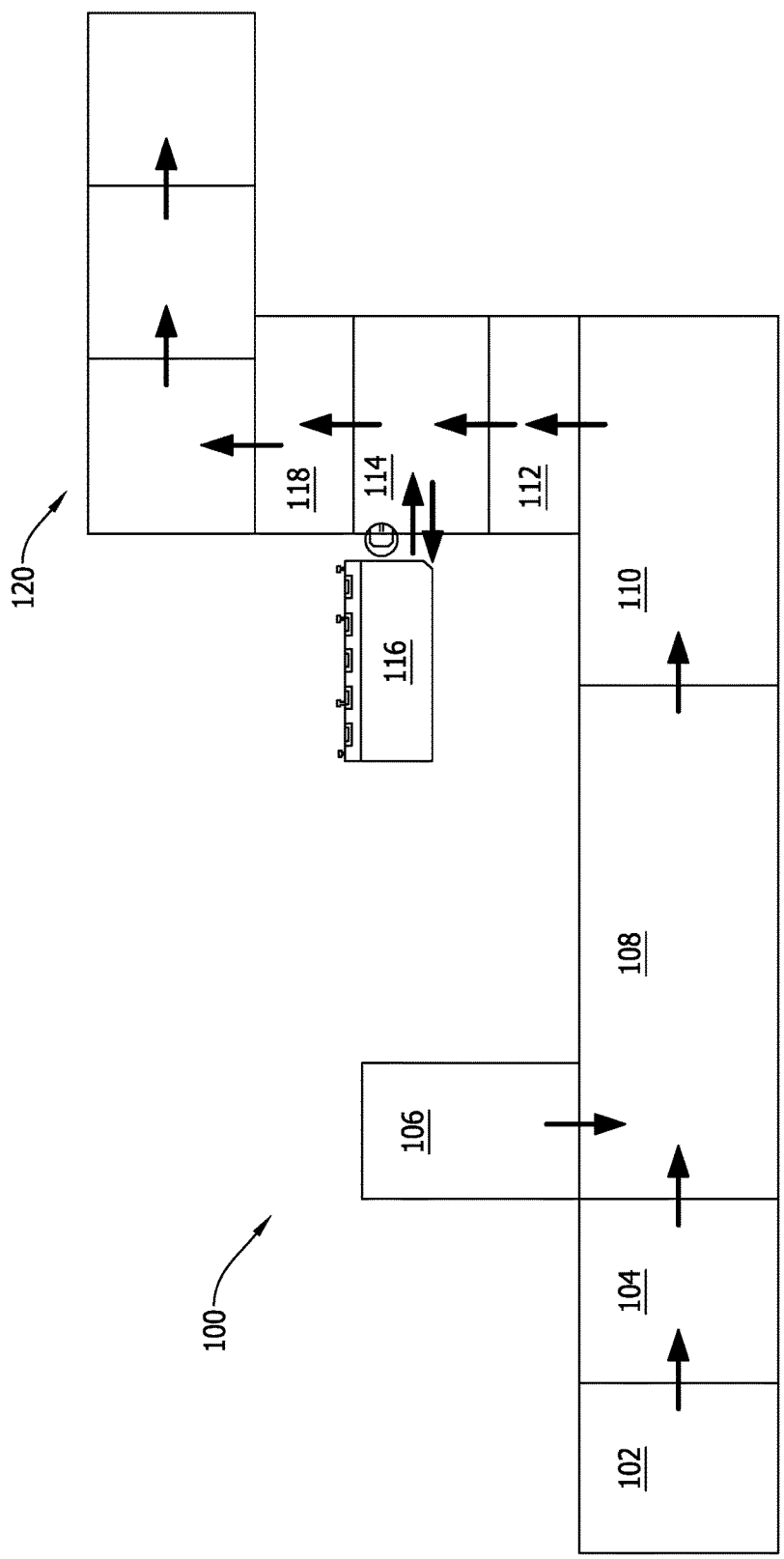
FIG. 1 is a schematic view of a system for producing radionuclide generators.

FIG. 1 is a schematic view of a system 100 for manufacturing radionuclide generators. The system 100 shown in FIG. 1 may be used to produce various radionuclide generators, including, for example and without limitation, Technetium generators, Indium generators, and Strontium generators. The system 100 of FIG. 1 is particularly suited for producing Technetium generators. A Technetium generator is a pharmaceutical drug and device used to create sterile injectable solutions containing Tc-99m, an agent used in diagnostic imaging with a relatively short 6 hour radiological half-life, allowing the Tc-99m to be relatively quickly eliminated from human tissue. Tc-99m is "generated" via the natural decay of Molybdenum ("Mo-99"), which has a 66 hour half-life, which is desirable because it gives the generator a relatively long two week shelf life. During generator operation (i.e., elution with a saline solution), Mo-99 remains chemically bound to a core alumina bed (i.e., a retaining media) packed within the generator column, while Tc-99m washes free into an elution vial, ready for injection into a patient. While the system 100 is described herein with reference to Technetium generators, it is understood that the system 100 may be used to produce radionuclide generators other than Technetium generators.

As shown in FIG. 1, the system 100 generally includes a plurality of stations. In the example embodiment, the system 100 includes a cask loading station 102, a formulation station 104, an activation station 106, a fill/wash station 108, an autoclave loading station 110, an autoclave station 112, an autoclave unloading station 114, a quality control testing station 116, a shielding station 118, and a packaging station 120.

The cask loading station 102 is configured to receive and handle casks or containers of radioactive material, such as a parent radionuclide, and transfer the radioactive material to the formulation station 104. Radioactive material may be transported in secondary containment vessels and flasks that need to be removed from an outer cask prior to formulation. The cask loading station 102 includes suitable tooling and mechanisms to extract secondary containment vessels and flasks from outer casks, as well as transfer of flasks to the formulation cell. Suitable devices that may be used in the cask loading station include, for example and without limitation, telemanipulators.

At the formulation station 104, the raw radioactive material (i.e., Mo-99) is quality control tested, chemically treated if necessary, and then pH adjusted while diluting the raw radioactive material to a desired final target concentration. The formulated radioactive material is stored in a suitable containment vessel (e.g., within the formulation station 104).

Column assemblies containing a column of retaining media (e.g., alumina) are activated at the activation station 106 to facilitate binding of the formulated radioactive material with the retaining media. In some embodiments, column assemblies are activated by eluting the column assemblies with a suitable volume of HCl at a suitable pH level. Column assemblies are held for a minimum wait time prior to charging the column assemblies with the parent radionuclide.

Following activation, column assemblies are loaded into the fill/wash station 108 using a suitable transfer mechanism (e.g., transfer drawer). Each column assembly is then charged with parent radionuclide by eluting formulated radioactive solution (e.g., Mo-99) from the formulation station 104 through individual column assemblies using suitable liquid handling systems (e.g., pumps, valves, etc.). The volume of formulated radioactive solution eluted through each column assembly is based on the desired Ci activity for the corresponding column assembly. The volume eluted through each column assembly is equivalent to the total Ci activity identified at the time of calibration for the column assembly. For example, if a volume of formulated Mo-99 required to make a 1.0Ci generator (at time of calibration) is 'X', the volume required to make a 19.0Ci generator is simply 19 times X. After a minimum wait time, the charged column assemblies are eluted with a suitable volume and concentration of acetic acid, followed by an elution with a suitable volume and concentration of saline to "wash" the column assemblies. Column assemblies are held for a minimum wait time before performing assays on the column assemblies.

The charged and washed column assemblies (or radionuclide generators) are then transferred to the autoclave load station 110, in which assays are taken from each column assembly to check the amount of parent and daughter radionuclide produced during elution. Each column assembly is eluted with a suitable volume of saline, and the resulting solution is assayed to check the parent and daughter radionuclide levels in the assay. Where the radioactive material is Mo-99, the elutions are assayed for both Tc-99m and Mo-99. Column assemblies having a daughter radionuclide (e.g., Tc-99m) assay falling outside an acceptable range calculation are rejected. Column assemblies having a parent radionuclide (e.g., Mo-99) breakthrough exceeding a maximum acceptable limit are also rejected. As described further herein, systems and methods of the present disclosure facilitate assaying elutions of radionuclide generators without the use of transfer vials or other liquid containers that require transfer to a radiation detection device. For example, embodiments of the systems and methods described herein facilitate eluting a radionuclide generator directly into the collection reservoir of a radiation detection device.

Following the assay process, tip caps are applied to the outlet port and the fill port of the column assembly. Column assemblies may be provided with tip caps already applied to the inlet port. If the column assembly is not provided with a tip cap pre-applied to the inlet port, a tip cap may be applied prior to, subsequent to, or concurrently with tip caps being applied to the outlet port and the fill port. Assayed, tip-capped column assemblies are then loaded into an autoclave sterilizer located in the autoclave station 112 for terminal sterilization. The sealed column assemblies are subjected to an autoclave sterilization process within the autoclave station 112 to produce terminally-sterilized column assemblies.

Following the autoclave sterilization cycle, column assemblies are unloaded from the autoclave station 112 into the autoclave unloading station 114. Column assemblies are then transferred to the shielding station 118 for shielding.

Some of the column assemblies are transferred to the quality control testing station 116 for quality control. In the example embodiment, the quality control testing station 116 includes a QC testing isolator that is sanitized prior to QC testing, and maintained at a positive pressure and a Grade A clean room environment to minimize possible sources of contamination. Column assemblies are aseptically eluted for in-process QC sampling, and subjected to sterility testing within the isolator of the quality control testing station 116. Tip caps are reapplied to the inlet and outlet needles of the column assemblies before the column assemblies are transferred back to the autoclave unloading station 114.

The system 100 includes a suitable transfer mechanism for transferring column assemblies from the autoclave unloading station 114 (which is maintained at a negative pressure differential, Grade B clean room environment) to the isolator of the quality control testing station 116. In some embodiments, column assemblies subjected to quality control testing may be transferred from the quality control testing station 116 back to the autoclave unloading station 114, and can be re-sterilized and re-tested, or re-sterilized and packaged for shipment. In other embodiments, column assemblies are discarded after being subjected to QC testing.

In the shielding station 118, column assemblies from the autoclave unloading station 114 are visually inspected for container closure part presence, and then placed within a radiation shielding container (e.g., a lead plug). The radiation shielding container is inserted into an appropriate safe constructed of suitable radiation shielding material (e.g., lead, tungsten or depleted uranium). Shielded column assemblies are then released from the shielding station 118.

In the packaging station 120, shielded column assemblies from the shielding station 118 are placed in buckets pre-labeled with appropriate regulatory (e.g., FDA) labels. A label uniquely identifying each generator is also printed and applied to each bucket. A hood is then applied to each bucket. A handle is then applied to each hood.

The system 100 may generally include any suitable transport systems and devices to facilitate transferring column assemblies between stations. In some embodiments, for example, each of the stations includes at least one telemanipulator to allow an operator outside the hot cell environment (i.e., within the surrounding room or lab) to manipulate and transfer column assemblies within the hot cell environment. Moreover, in some embodiments, the system 100 includes a conveyance system to automatically transport column assemblies between the stations and/or between substations within one or more of the stations (e.g., between a fill substation and a wash substation within the fill/wash station 108).

In the example embodiment, some stations of the system 100 include and/or are enclosed within a shielded nuclear radiation containment chamber, also referred to herein as a "hot cell". Hot cells generally include an enclosure constructed of nuclear radiation shielding material designed to shield the surrounding environment from nuclear radiation. Suitable shielding materials from which hot cells may be constructed include, for example and without limitation, lead, depleted uranium, and tungsten. In some embodiments, hot cells are constructed of steel-clad lead walls forming a cuboid or rectangular prism. In some embodiments, a hot cell may include a viewing window constructed of a transparent shielding material. Suitable materials from which viewing windows may be constructed include, for example and without limitation, lead glass. In the example embodiment, each of the cask loading station 102, the formulation station 104, the fill/wash station 108, the autoclave loading station 110, the autoclave station, the autoclave unloading station 114, and the shielding station 118 include and/or are enclosed within a hot cell.

In some embodiments, one or more of the stations are maintained at a certain clean room grade (e.g., Grade B or Grade C). In the example embodiment, pre-autoclave hot cells (i.e., the cask loading station 102, the formulation station 104, the fill/wash station 108, the autoclave loading station 110) are maintained at a Grade C clean room environment, and the autoclave unloading cell or station 114 is maintained at a Grade B clean room environment. The shielding station 118 is maintained at a Grade C clean room environment. The packaging stations 120 are maintained at a Grade D clean room environment.

Additionally, the pressure within one or more stations of the system 100 may be controlled at a negative or positive pressure differential relative to the surrounding environment and/or relative to adjacent cells or stations. In some embodiments, for example, all hot cells are maintained at a negative pressure relative to the surrounding environment. Moreover, in some embodiments, the isolator of the quality control testing station 116 is maintained at a positive pressure relative to the surrounding environment and/or relative to adjacent stations of the system 100 (e.g., relative to the autoclave unloading station 114).

Figure 2:
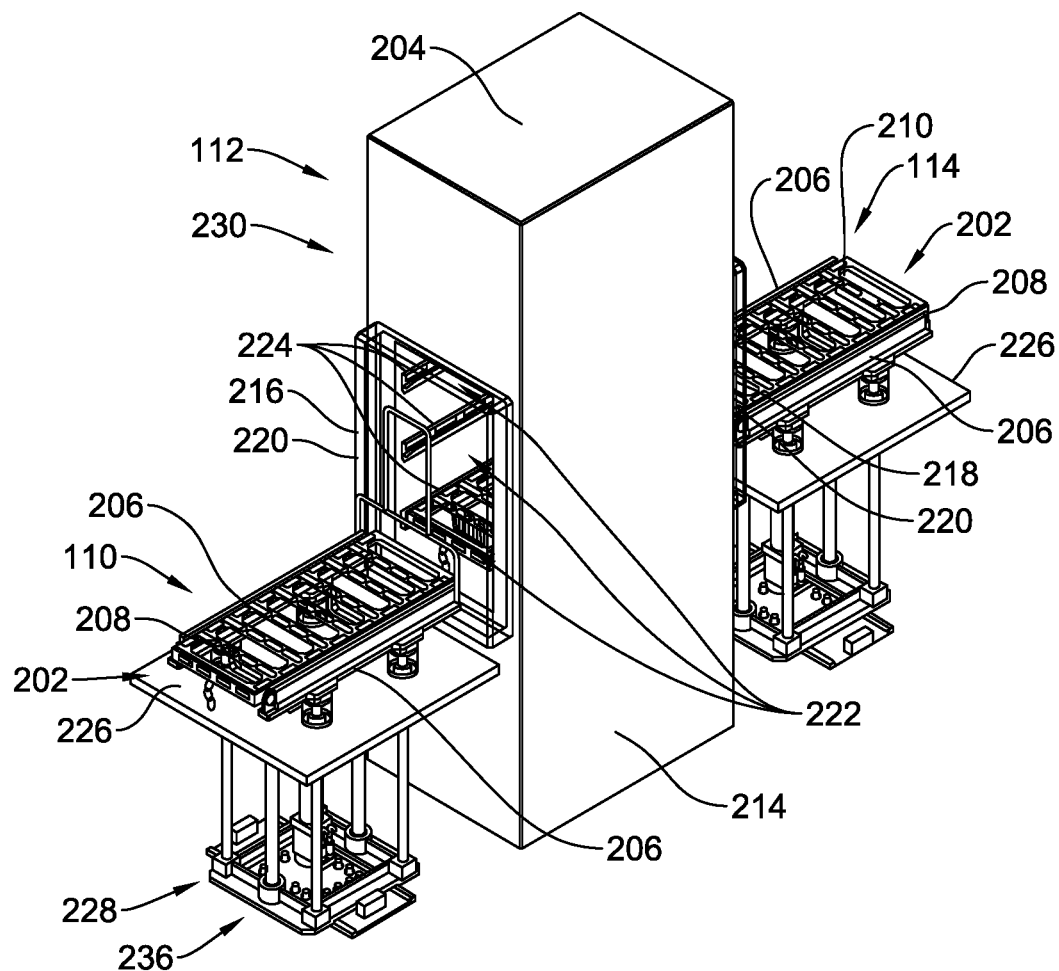
FIG. 2 is a perspective view of the autoclave loading station, the autoclave station, and the autoclave unloading station of a radionuclide generator production line shown in FIG. 1.
Figure 3:
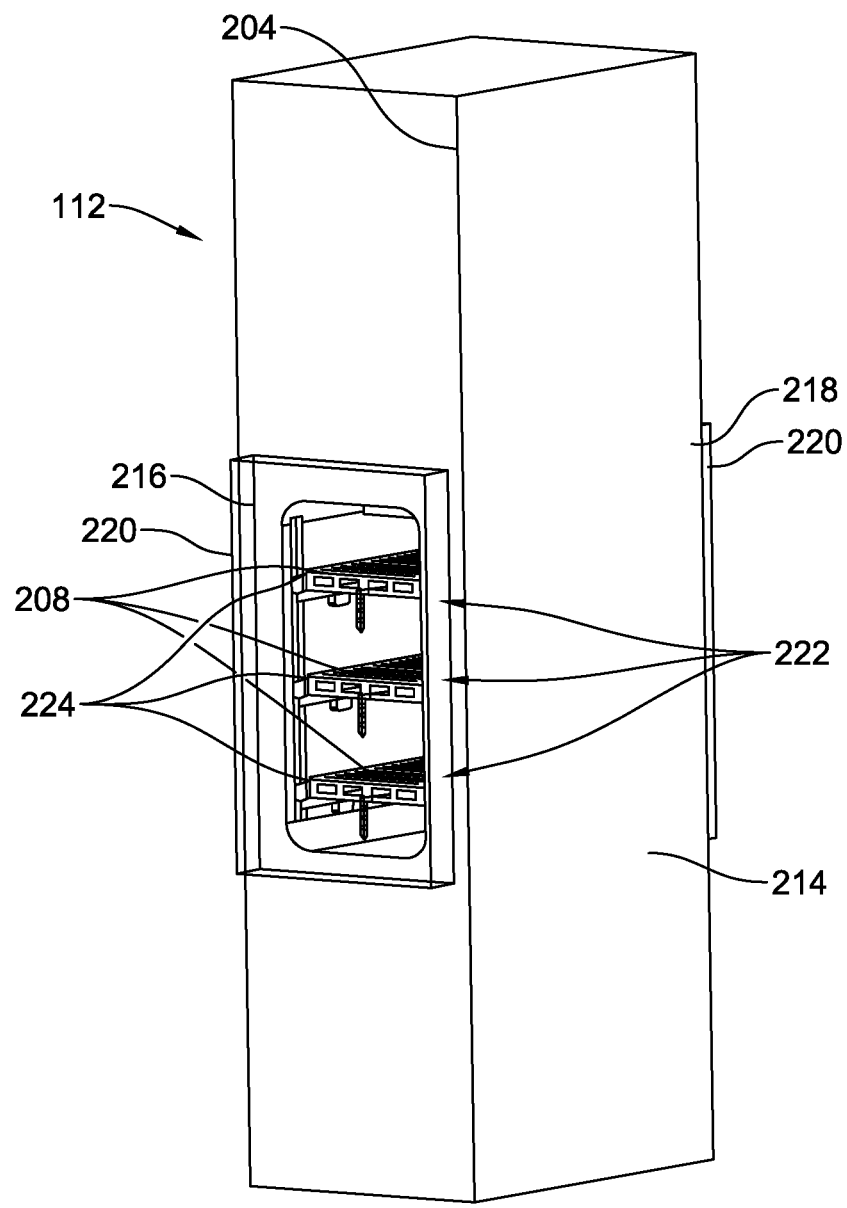
FIG. 3 is a perspective view of an autoclave station shown in FIG. 1.
Figure 4:
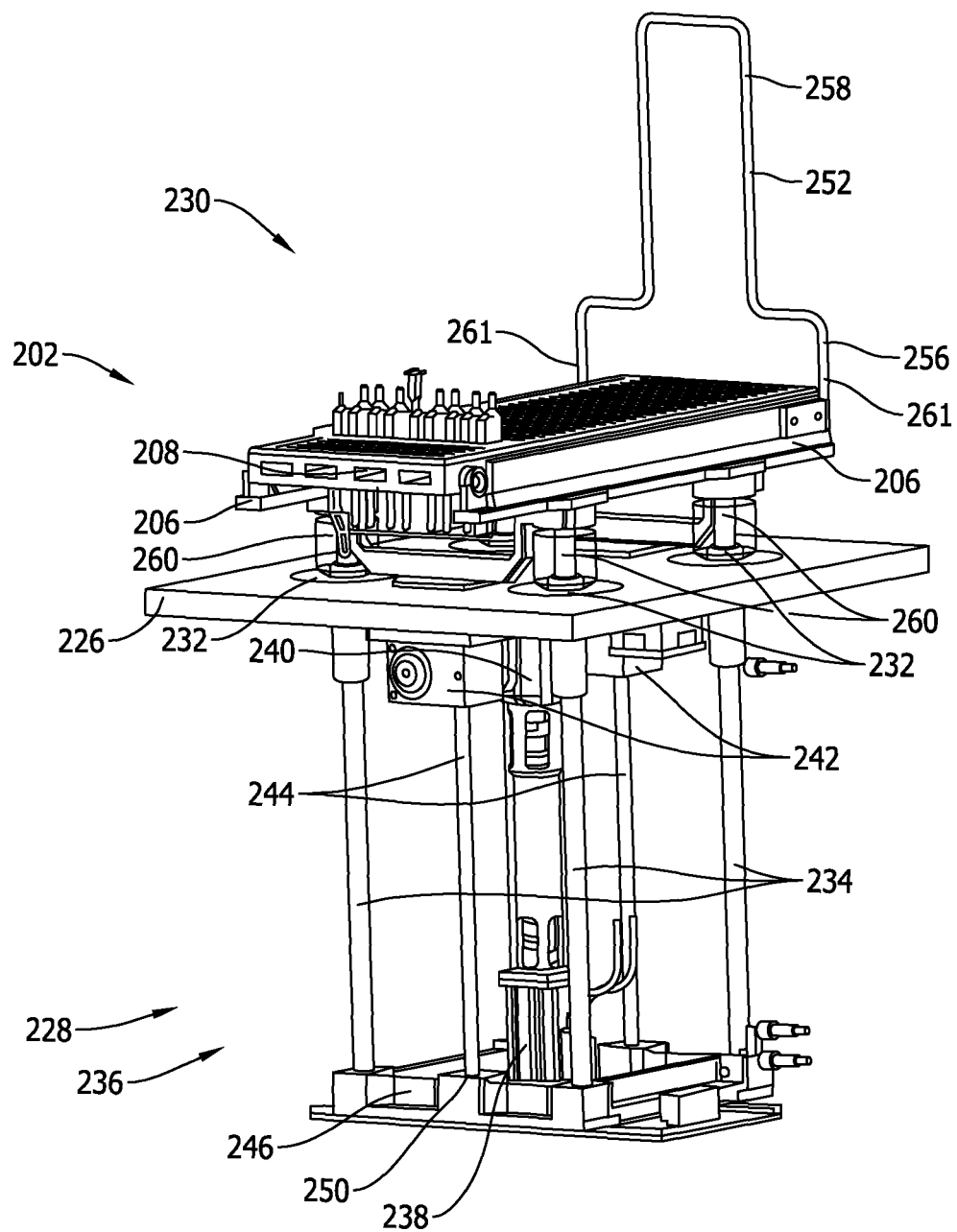
FIG. 4 is a perspective view of an autoclave loading/unloading elevator shown in FIG. 1.
Figure 5:
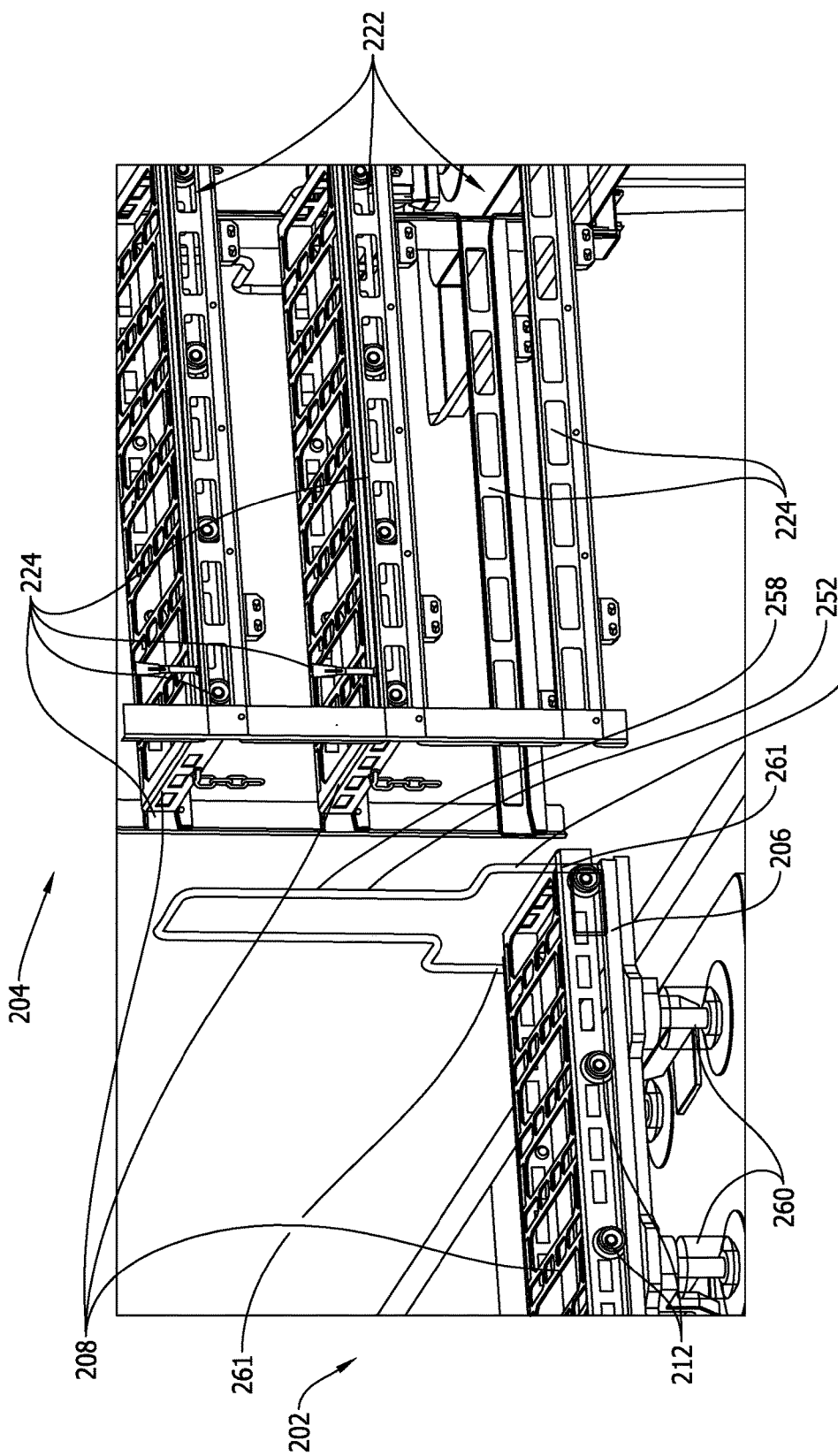
FIG. 5 is a perspective view of the autoclave loading station and sterilization stations shown in FIG. 1 with the autoclave sterilizer removed for clarity.

FIG. 2 is a perspective view of the autoclave loading station 110, the autoclave station 112, and the autoclave unloading station 114 of a radionuclide generator that may be produced with the system 10. FIG. 3 is a perspective view of the autoclave station 112. FIG. 4 is a perspective view of the autoclave loading station 110 and the autoclave unloading station 114. FIG. 5 is a perspective view of the autoclave loading station 110 and sterilization stations 222 with autoclave sterilizer 204 removed for clarity.

Although not illustrated in FIGS. 2-5, the components of the autoclave loading station 110, the autoclave station 112, and the autoclave unloading station 114 are enclosed within a hot cell. That is, the components of the autoclave loading station 110, the autoclave station 112, and the autoclave unloading station 114 are enclosed within an enclosure constructed of nuclear radiation shielding material designed to shield the surrounding environment from nuclear radiation. Additionally, in some embodiments, the autoclave loading station 110, the autoclave station 112, and the autoclave unloading station 114 is maintained at a Grade B or higher class clean room environment. That is, the autoclave unloading station 114 has a clean room classification of Grade B or higher.

As shown in FIG. 2, the autoclave loading station 110 and the autoclave unloading station 114 both include an autoclave loading/unloading elevator 202. The autoclave loading/unloading elevator 202 within the autoclave loading station 110 is positioned on the upstream (i.e., loading) side of an autoclave sterilizer 204. The autoclave loading elevator 202 includes two elevator cart rails 206 that receive a cart 208 containing up to eight racks 210 (with up to eight column assemblies per rack 210) from the fill/wash station 108. The cart 208 includes a plurality of wheels 212 that enable the cart 208 to roll from the autoclave loading station 110 to the autoclave loading station 110 and the autoclave unloading station 114. The cart 208 may be moved from the autoclave unloading station 114 to the autoclave loading station 110 and the autoclave unloading station 114.

The autoclave sterilizer 204 includes an outer casing 214, an entrance 216, an exit 218 and two doors 220. The autoclave sterilizer 204 also includes a plurality of sterilization stations 222 arranged vertically such that each sterilization station 222 is at a different height within the autoclave sterilizer 204. Each sterilization station 222 includes autoclave rails 224, each positioned within autoclave sterilizer 204. During the loading operation, the doors 220 open allowing the cart 208 to enter the autoclave sterilizer 204 through the entrance 216. The autoclave rails 224 receive the cart 208 from the autoclave loading station 110. Specifically, the cart 208 is rolled from the elevator cart rails 206 to the autoclave rails 224 using the autoclave loading/unloading mechanism. The doors 220 are closed and the sterilization process begins within the autoclave sterilizer 204. Autoclave sterilization generally includes exposing a column assembly, having a column loaded with parent radionuclide, to a saturated steam, or a steam-air mixture environment.

In this embodiment, the autoclave sterilizer 204 includes three sterilization stations 222. However, the autoclave sterilizer 204 is not limited to three sterilization stations 222 and may include any number of sterilization stations 222 that enable the autoclave sterilizer to operate as described herein including, for example and without limitation, up to five sterilization stations 222. Each sterilization station 222 supports one cart 208 and each cart 208 holds eight racks 210. Each rack 210 holds up to eight column assemblies. Thus, the autoclave sterilizer 204 sterilizes up to 192 column assemblies per sterilization process.

In other embodiments, each cart can hold up to twenty-four racks 210 and each rack 210 can hold up to eight column assemblies. Thus, the autoclave sterilizer 204 sterilizes up to 1200 column assemblies per sterilization process.

The autoclave loading/unloading elevator 202 within the autoclave unloading station 114 is positioned on the downstream (i.e., unloading) side of the autoclave sterilizer 204. The elevator cart rails 206 receive the cart 208 from the autoclave sterilizer 204. The cart 208 may be removed from the autoclave sterilizer 204, and the racks 210 transferred to an autoclave unloading shuttle (not shown) using an autoclave unloading mechanism including, for example and without limitation, manual, automated, or semi-automated transfer mechanisms such as telemanipulators and pneumatic cylinders.

Figure 6:
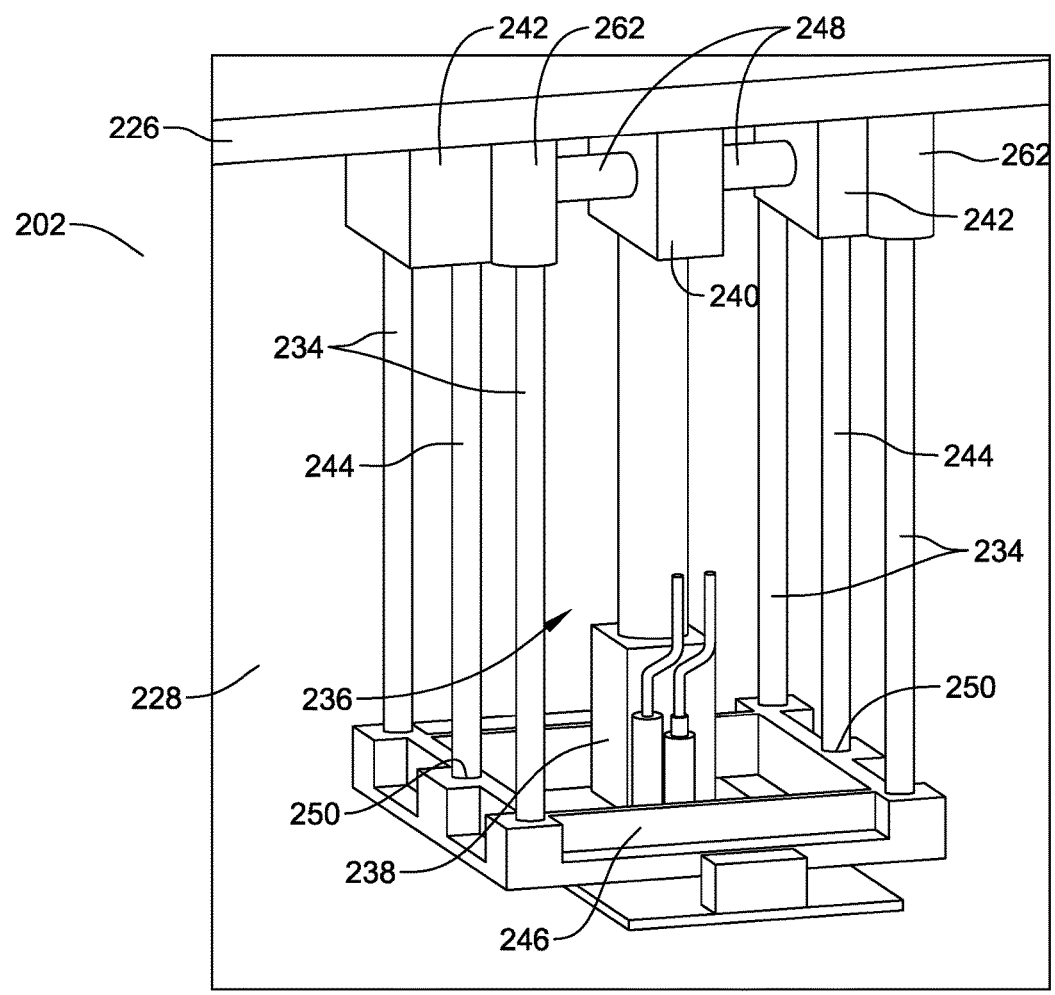
FIG. 6 is a perspective view of an underside of the autoclave loading/unloading elevator shown in FIG. 1.
Figure 7:
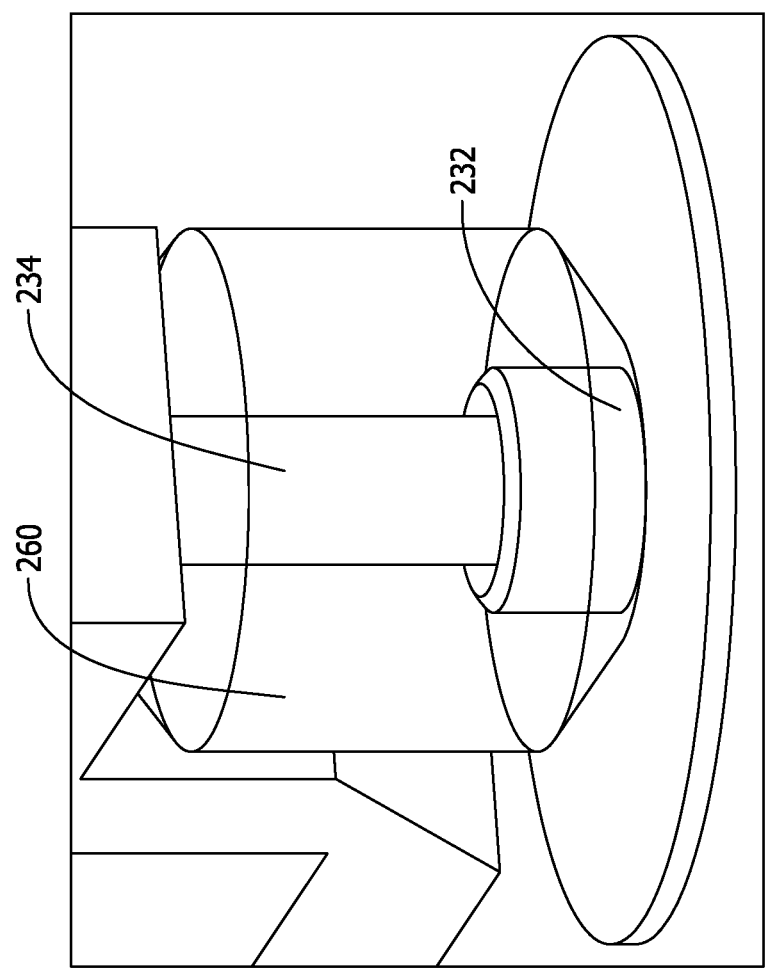
FIG. 7 is a perspective view of a bellows sleeves shown in FIG. 4.
Figure 8:
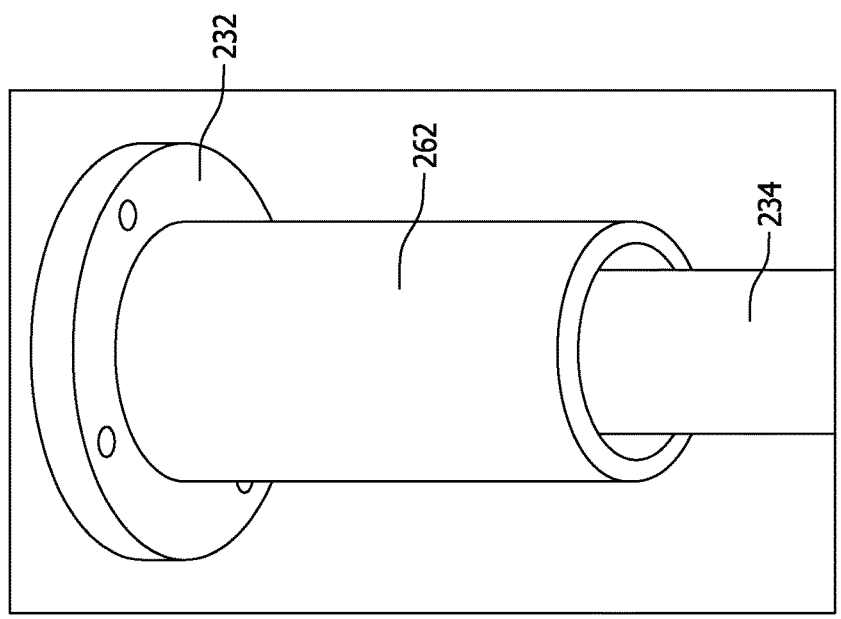
FIG. 8 is a perspective view of a bearing shown in FIG. 4.

FIG. 6 is a perspective view of an underside of the autoclave loading/unloading elevator 202. FIG. 7 is a perspective view of a bellows sleeves. FIG. 8 is a perspective view of a bearing.

As shown in FIG. 6, the autoclave loading/unloading elevator 202 includes a table top 226 that separates a maintenance space 228 below the table top 226 from a processing space 230 above the table top 226. The table top 226 includes a plurality of penetrations 232 that enable a plurality of elevator guide rails 234 to extend through the table top 226. The elevator guide rails 234 are coupled to the elevator cart rails 206 and are configured to raise and lower the elevator cart rails 206. In this embodiment, the autoclave loading/unloading elevator 202 includes four elevator guide rails 234. However, the autoclave loading/unloading elevator 202 may include any number of elevator guide rails 234 that enable the autoclave loading/unloading elevator 202 to operate as described herein.

The autoclave loading/unloading elevator 202 also includes an elevation system 236 positioned below table top 226 within maintenance space 228. The elevation system 236 is configured to raise and lower the elevator guide rails 234 which are configured to raise and lower the elevator cart rails 206. The elevation system 236 includes a motor 238, a center worm drive 240, two right-angle gear boxes 242, two screws 244, and a platform 246. The elevation system 236 also includes a programmable logic controller (hereinafter "PLC") system (not shown) configured to control the elevation system 236. In this embodiment, the motor 238 includes a servomotor. Servomotors use resolver feedback and polyurethane cabling, and are immune to high radiation effects. However, the motor 238 can include any motor that enables the elevation system 236 to operate as described herein.

In this embodiment, the motor 238 is coupled to the center worm drive 240 that is coupled to the two right-angle gear boxes 242 by a pair of shafts 248. The two right-angle gear boxes 242 are each coupled to a respective screw 244 which each extend downward from the two right-angle gear boxes 242 to the platform 246. The screws 244 each include a raised helical thread (not shown) running around the screw 244 and extending along a length of the screw 244. The platform 246 includes two threaded holes 250 each including a depressed helical thread (not shown) running around the inside of threaded holes 250. The elevator guide rails 234 extend vertically from the platform 246 through the table top 226 to the elevator cart rails 206.

During operation, the motor 238 provides the power for elevating the cart 208. The center worm drive 240 translates the motion of the motor 238 through the shafts 248 to the two right-angle gear boxes 242. The two right-angle gear boxes 242 each rotate a respective screw 244. Rotation of the screw 244 causes the complementary helical treading on the screw 244 and in the threaded holes 250 to raise or low the platform 246. The platform 246 raises or lowers the elevator guide rails 234 which raise or lower the elevator cart rails 206 and the cart 208. In one embodiment, motor 238 raises the cart 208 at a speed of about 0.1-1 inch per second, or about 0.2-0.5 inches per second, or about 0.25 inches per second.

As shown in FIG. 5, the sterilization stations 222 are arranged vertically within the autoclave sterilizer 204. Each sterilization station 222 has a height that is different from the other sterilization stations 222. As such, the elevation system 236 raises or lowers the cart 208 to a predetermined height corresponding to each sterilization station 222. Only when the elevation system 236 raised or lowered the cart 208 to the predetermined height corresponding to each sterilization station 222 can the cart 208 be rolled on to the autoclave rails 224. The PLC system controls the elevation system 236 such that the elevation system 236 only raises or lowers the cart 208 to the predetermined height corresponding to each sterilization station 222. Additionally, the motor 238 includes a brake (not shown) that prevents the cart 208 from descending if power is no longer supplied to the motor 238. In this embodiment, the lowest sterilization station 222 is approximately 12 inches above table top 226. Each sterilization station 222 above the lowest sterilization station 222 is approximately 8 inches above the previous sterilization station 222 such that there is at least about 0.1-0.5, or about 0.2-0.4 or about 0.25 inch clearance between loaded carts 208 within the autoclave sterilizer 204.

Referring still to FIG. 5, the autoclave loading/unloading elevator 202 includes an unloading prevention bar 252 configured to prevent an operator from unloading a cart 208 from the autoclave sterilizer 204 before the elevation system 236 is prepared to receive the cart 208. In this embodiment, the unloading prevention bar 252 includes a bent bar with a wide portion 256 and a narrow portion 258. Each end 261 of the bent bar 252 is coupled to one of the elevator cart rails 206 and the bent bar 252 extends vertically from the elevator cart rails 206. The wide portion 256 is located near the elevator cart rails 206 and is wide enough to allow the cart 208 to pass from the elevator cart rails 206 to the autoclave sterilizer 204. The narrow end 258 is located away from the elevator cart rails 206 and is narrow enough to prevent a cart 208 in the autoclave sterilizer 204 from falling onto a cart 208 on the elevator cart rails 206 when the elevation system 236 is not at the predetermined height corresponding to the sterilization station 222. In some embodiments, the wide end 256 is about 6-10 inches, or about 8 inches tall, and the narrow end 258 is about 15-25 inches tall or about 20 inches tall. The wide end 256 is between about 15-25 inches wide or about 18 inches wide, and the narrow end 258 is about 8-10 inches wide or about 9 inches wide.

As shown in FIG. 4, autoclave loading/unloading elevator 202 includes a plurality of bellow sleeves 260 and a plurality of bearings 262. The bellow sleeves 260 surround the elevator guide rails 234 above the table top 226 within the processing space 230. The bellow sleeves 260 extend with the elevator guide rails 234 in the vertical direction as the elevation system 236 raises and lowers the cart 208. The bellow sleeves 260 seal the penetrations 232 and ensure the processing space 230 is separated from the maintenance space 228. This ensures that the processing space 230 can be sanitized with Vaporous Hydrogen Peroxide (VHP) without dirty air leakage from the maintenance space 228 below the table top 226, and without exposure of lubricated elevator shafts within the processing space 230. Bellow sleeves 260 are made of Viton, ethylene propylene diene terpolymer rubber (EPDM), or polyvinyl chloride (PVC). However, the bellow sleeves 260 can be made of any material that enables the elevation system 236 to operate as described herein.

The elevator guide rails 234 extend through the table top 226 through the bearings 262. The bearings 262 ensure the elevator guide rails 234 move smoothly up and down, and that the elevator guide rails 234 will not mechanically bind during movement.

Figure 9:
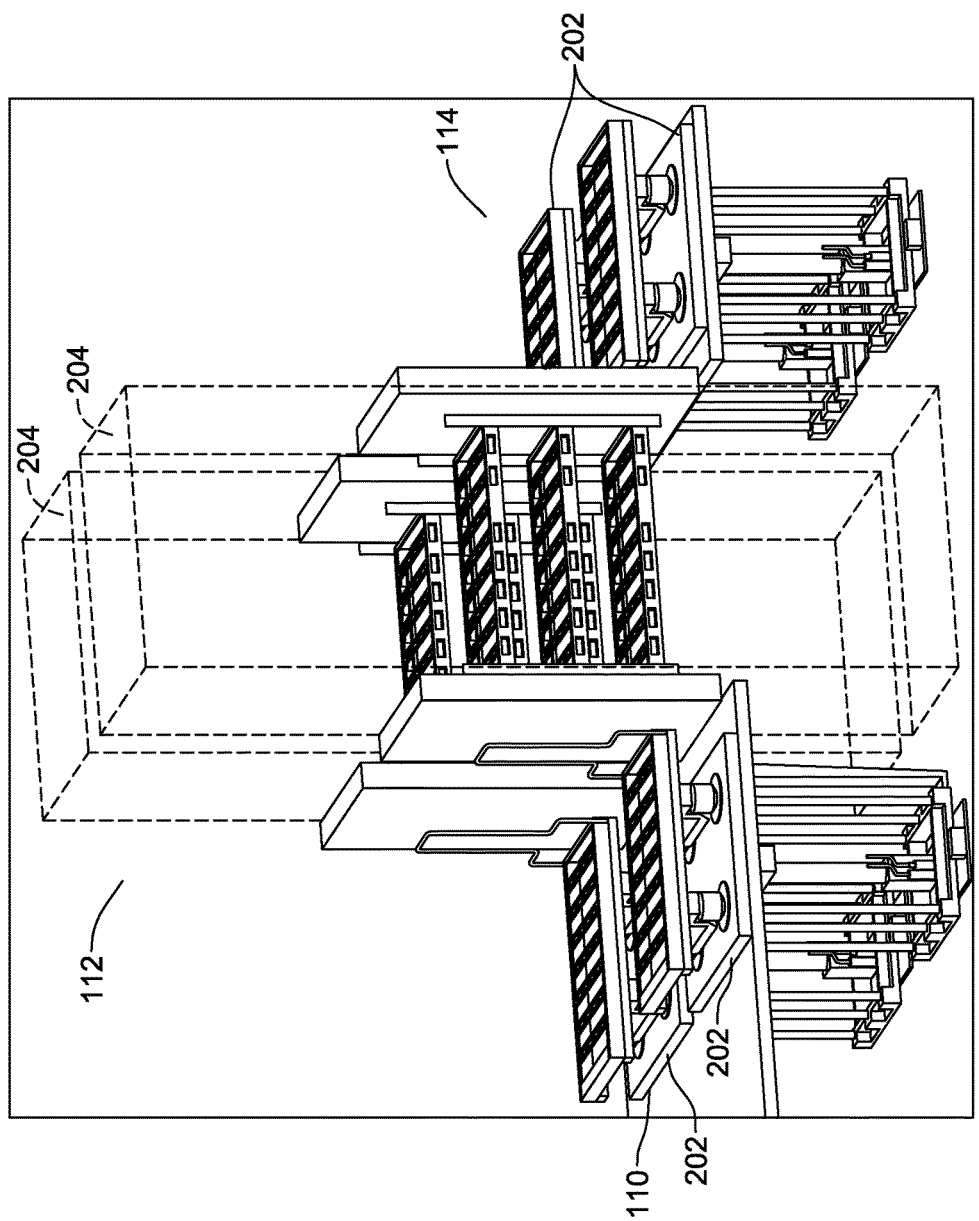
FIG. 9 is a perspective view of two autoclave stations of a radionuclide generator shown in FIG. 1.

FIG. 9 is a perspective view of two autoclave loading stations 110, two autoclave stations 112, and two autoclave unloading stations 114. In this embodiment, system 100 includes two autoclave loading stations 110, two autoclave stations 112, and two autoclave unloading stations 114 for redundancy.

An example system suitable for carrying out methods of this disclosure includes an autoclave station 112 including at least one autoclave sterilizer 204, an autoclave loading station 110 adjoining the autoclave station 112, and an autoclave unloading station 114 adjoining the autoclave station 112. In some embodiments, a hot cell encloses the autoclave loading station 110, the autoclave station 112, and the autoclave unloading station 114. Additionally, in some embodiments, autoclave loading station 110 and the autoclave unloading station 114 include an elevation system 236 configured to raise and lower a cart 208. Moreover, in some embodiments, the autoclave loading station 110 and the autoclave unloading station 114 include telemanipulators configured to load and unload the carts 208 from the autoclave sterilizer 204.

The systems and methods of the present disclosure provide several advantages over known autoclave sterilizer loading and unloading systems. For example, embodiments of the disclosed systems and methods facilitate raising and lowering racks of column assemblies. Additionally, embodiments of the disclosed systems and methods facilitate loading/unloading the racks into and from an autoclave safely, given limited mechanical reach within the hot cell environment. Embodiments of the present disclosure include loading/unloading elevators which raise and lower racks of column assemblies, rails which facilitate rolling carts of column assemblies into the autoclave, a motor to power the loading/unloading elevators, and PLC to control the loading/unloading elevators. The loading/unloading elevators enable the autoclave sterilizer to include additional stacked sterilization stations. The additional sterilization stations allow the autoclave sterilizer to sterilize more column assemblies, improving the throughput of the generator manufacturing process. The elevator design allows completely sealed separation between a clean space above the tabletop that can be sanitized for pharmaceutical manufacturing, and a mechanical space below the tabletop.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A loading and unloading elevator for an autoclave sterilizer in a radioactive environment, the loading and unloading elevator comprising:
   a table top separating a processing space from a maintenance space;
   an elevation system positioned within the maintenance space;
   at least two cart rails configured to support a cart, the cart rails positioned within the processing space; and
   a plurality of loading elevator rails coupled to the cart rails, the loading elevator rails extend from the elevation system within the maintenance space through the table top to the processing space, wherein the loading elevator rails are configured to adjust the height of the cart rails.

2. The loading and unloading elevator of claim 1, wherein the elevation system is configured to adjust the height of the loading elevator rails and the cart rails.

3. The loading and unloading elevator of claim 2, wherein the elevation system comprises a platform coupled to the loading elevator rails, wherein the platform is configured to adjust the height of the loading elevator rails and the cart rails.

4. The loading and unloading elevator of claim 3, wherein the elevation system further comprises a motor coupled to the platform, wherein the motor is configured to adjust the height of the platform, the loading elevator rails, and the cart rails.

5. The loading and unloading elevator of claim 4, further comprising a plurality of bearings extending through the table top, wherein the bearings guide the loading elevator rails through the table top.

6. The loading and unloading elevator of claim 5, further comprising a plurality of bellow sleeves, each bellow sleeve surrounds one loading elevator rail and extends from the bearings to the cart rails.

7. The loading and unloading elevator of claim 6, wherein the elevation system is configured to adjust a height of the cart to a plurality of predetermined heights.

8. The loading and unloading elevator of claim 7, wherein the elevation system further comprises a programmable logic controller configured to control the motor, wherein the programmable logic controller is configured to adjust the height of the cart to each of the predetermined heights.

9. The loading and unloading elevator of claim 8, further comprising a worm drive, two right-angle gearboxes, and two screws, the worm drive being coupled to the motor and to the two right-angle gearboxes, each right-angle gearbox being coupled to one of the screws, the screws being coupled to the platform, wherein a motor turns the worm drive, the worm drive turns the two right-angle gearboxes, each right-angle gearbox turns one of the screws, and the screws adjust a height of the platform.

* * * * *